United States Patent [19]

Ishiguro et al.

[11] Patent Number: 5,150,715
[45] Date of Patent: Sep. 29, 1992

[54] ULTRASOUND-IMAGING DIAGNOSTIC SYSTEM

[75] Inventors: Masaaki Ishiguro; Toshizumi Tanaka; Yukio Takagi, all of Omiya, Japan

[73] Assignee: Fuji Photo Optical Co., Ltd., Omiya, Japan

[21] Appl. No.: 683,295

[22] Filed: Apr. 10, 1991

[30] Foreign Application Priority Data

Apr. 18, 1990 [JP] Japan .................. 2-100395
Apr. 18, 1990 [JP] Japan .................. 2-100396
Apr. 18, 1990 [JP] Japan .................. 2-100397

[51] Int. Cl.⁵ ................................ A61B 8/12
[52] U.S. Cl. ................................ 128/662.06
[58] Field of Search ............... 128/660.03, 662.06

[56] References Cited

U.S. PATENT DOCUMENTS

| | | | |
|---|---|---|---|
| 3,779,234 | 12/1973 | Eggleton et al. | 128/662.06 |
| 4,466,444 | 8/1984 | Baba | 128/662.06 |
| 4,802,487 | 2/1989 | Martin et al. | 128/662.06 |
| 4,928,699 | 5/1990 | Sasai | 128/662.06 |

Primary Examiner—Francis Jaworski
Attorney, Agent, or Firm—Oblon, Spivak, McClelland, Maier & Neustadt

[57] ABSTRACT

Described herein is an ultrasound imaging system which essentially comprises: an ultrasound probe having an elongated flexible body rotatably supporting an ultrasound transducer on a tip end portion thereof; an operating unit including means for scanning the ultrasound probe; a flexible cord having one end thereof securely fixed to the operating unit and the other end detachably connected to an ultrasound image observation terminal; and a rotary connector composed of relatively rotatable members and inserted in the wiring leading from the ultrasound transducer to a connector means connecting the flexible cord to the ultrasound image observation terminal.

6 Claims, 6 Drawing Sheets

FIG.4
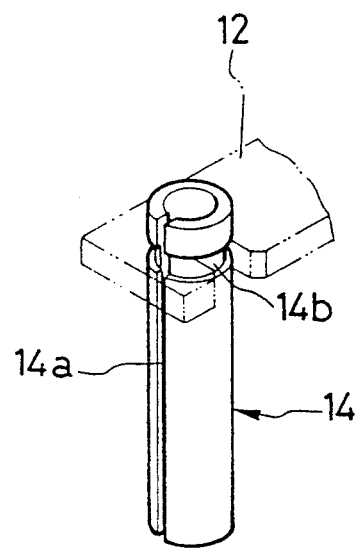
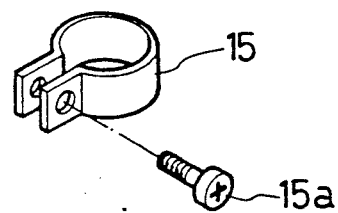

ance, in U.S. Pat. No. 4,802,487, there have

ULTRASOUND-IMAGING DIAGNOSTIC SYSTEM

BACKGROUND OF THE INVENTION

1. Field of the Invention

This invention relates to an ultrasound-imaging system employing an ultrasound probe to be inserted into patient's body for ultrasound examination or diagnosis.

2. Prior Art

The ultrasound imaging system is generally composed of an ultrasound transmitter-receiver or transducer and an ultrasound image observation terminal, the observation terminal including ultrasound signal transmission and reception circuits, a signal processing circuit for processing the ultrasound echo signals received by the reception circuit, and a monitor for viewing an ultrasound image. The ultrasound imaging systems of this sort are widely used in the medical field, transmitting ultrasound energy into a body through an ultrasound transducer and transferring return signals to the signal processing circuit of the ultrasound observation terminal to display the information concerning intracorporeal tissue as an ultrasound image on the monitor screen.

In this connection, for the purpose of improving the accuracy and functions of the ultrasound examination or diagnosis, there have come into use ultrasound examination systems which are arranged to insert an ultrasound transducer into patient's body to transmit and receive ultrasound signals at a position close to an intracorporeal structure to be examined or diagnosed. Further, as proposed in U.S. Pat. No. 4,802,487, there have also been developed endoscopic ultrasound imaging systems which, for three-dimensional examination, provides, in addition to the optical examination and diagnosis through an endoscope, the ultrasound information on the tissue of an intracavitary structure of interest by inserting into patient's body a narrow ultrasound probe or catheter having an ultrasound transducer at its tip end under guidance of an endoscope. For this purpose, the ultrasonic probe is inserted into a biopsy instrument channel which is usually provided in the endoscope for insertion of forceps or other treating instruments, protruding the ultrasound transducer from the tip end of the biopsy channel for transmission and reception of ultrasound energy.

In such ultrasound examination or diagnosis, it is the general practice to bring the ultrasound transducer into intimate contact with an intracavitary wall or the like or to position the ultrasound transducer to face an intracavitary wall through intervention of an ultrasound transmissive medium like water, holding the ultrasound transducer in certain direction and posture with respect to the intracavitary wall during transmission and reception of ultrasound waves. Besides, in case of an ultrasound imaging system using an endoscopically inserting ultrasound probe, it is necessary to adjust the direction and posture of the ultrasound transducer through remote control. For this purpose, a manual rotating mechanism is provided in association with a rear end portion of the catheter or insert section of the probe outside the proximal end of the biopsy channel of the endoscope, torsionally turning the catheter through manipulation of the rotating mechanism for controlling the direction and posture of the ultrasound transducer. In case of a mechanical radial scan type, the insert section is connected to a mechanical rotational drive means.

However, when torsionally turning the insert section of the probe in the biopsy channel of the endoscope directly by a manual operation, a difficulty is often encountered in transmitting the turning moment smoothly to the ultrasound transducer due to inferior operationability particularly in controlling the direction of the transducer. Besides, as a cable from the ultrasound transducer is normally blocked against rotation at its proximal end which is connected to an operating unit, the cable is twisted in the proximal portion when it is operated to rotate the ultrasound transducer, instabilizing and causing positional deviations of the ultrasound transducer by the righting force of the twisted cable portion. Accumulation of such twist takes place when the operation is repeated, inviting further deteriorations in controllability and, in case of accumulation of a large number of twists, causing a disconnection in wiring cable which is inserted in a sheath material of the probe.

Further, in controlling the direction and posture of the ultrasound transducer, it is often the case that the operator of the ultrasound imaging system does not pay much attention to the twisting of the cable. For controlling the posture of the ultrasound transducer, it is the general practice to turn the cable in a certain predetermined direction, so that the cable is usually twisted to a considerable degree, in spite of the instabilization of the position and posture of the ultrasound transducer and high possibility of wire disconnection in the cable. In this regard, it is conceivable to restrict the rotational angle of the cable, which however gives rise to a problem of deterioration of controllability in controlling the direction and posture of the ultrasound transducer.

SUMMARY OF THE INVENTION

In view of the problems or difficulties stated above, the present invention has as its object the provision of an ultrasound-imaging examination system which is arranged to prevent twisting of a proximal portion of a cable from an ultrasonic transducer in rotating operations which control the direction and posture of the ultrasound transducer.

In accordance with the present invention, there is provided, for achieving the above-stated objective, an ultrasound imaging system which essentially includes: an ultrasound probe having an elongated flexible body rotatably supporting an ultrasound transducer on a tip end portion thereof; an operating unit having means for scanning the ultrasound probe; a flexible cord having one end thereof securely fixed to the operating unit and the other end detachably connected to an ultrasound image observation terminal; and a rotary connector composed of relatively rotatable members and inserted in the wiring from the ultrasound transducer to a connector means between the flexible cord and the ultrasound image observation terminal.

The above and other objects, features and advantages of the invention will become apparent from the following description and the appended claims, taken in conjunction with the accompanying drawings which show by way of example a preferred embodiment of the invention.

BRIEF DESCRIPTION OF THE DRAWINGS

In the accompanying drawings:

FIG. 4 is an outer view of a connector pipe;

DESCRIPTION OF PREFERRED EMBODIMENTS

Figure 1:
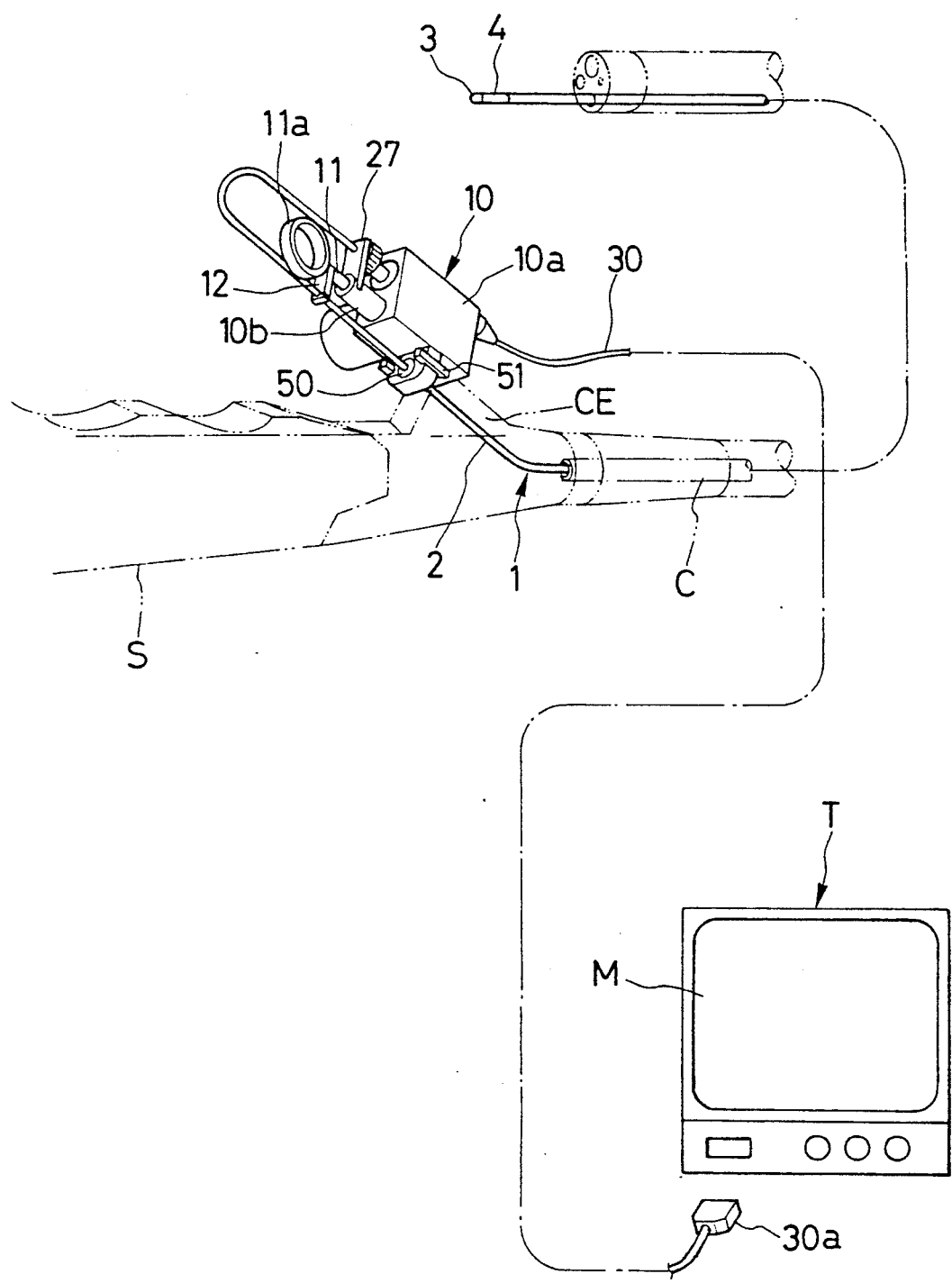
FIG. 1 is a schematic view of an ultrasound-image diagnostic system embodying the present invention, showing the general construction of the system.

Hereafter, the invention is described in greater detail by way of the preferred embodiment shown in the drawings.

Referring to FIG. 1, there is shown the general arrangement of an ultrasound diagnostic system according to the present invention, in which indicated at 1 is an ultrasound probe and at 10 is an operating unit. The ultrasound probe 1 includes an elongated flexible insert body 2, a rigid tip member 3 attached to the fore end of the insert body 2, and an ultrasound transducer 4 consisting of a single vibratory element mounted in the rigid tip member 3 to serve as an ultrasound signal transducer. The operating unit 10 constitutes operating means for scanning the afore-mentioned ultrasound transducer 4 and at the same time as a position sensor means for detecting the position of the ultrasound transducer 4 within the scanning range thereof. The ultrasound transducer 4 of the probe 1 and the position sensor mechanism of the operating unit 10 are electrically connected to an ultrasound image observation terminal T through a flexible cord 30 for transmission of signals therebetween.

The rigid tip member 3 at the fore end of the insert body 2 of the ultrasound probe 1 is rotatable relative to the insert body 2, and the ultrasound transducer 4 has an ultrasound signal transmission-reception surface 4a faced toward an opening which is formed at one side of the rigid tip member 3. In this instance, the ultrasound transducer 4 is moved linearly in a predetermined direction to scan an intracavitary wall portion over a predetermined length to obtain an ultrasound image of a cross section of intracorporeal tissue.

Figure 2:
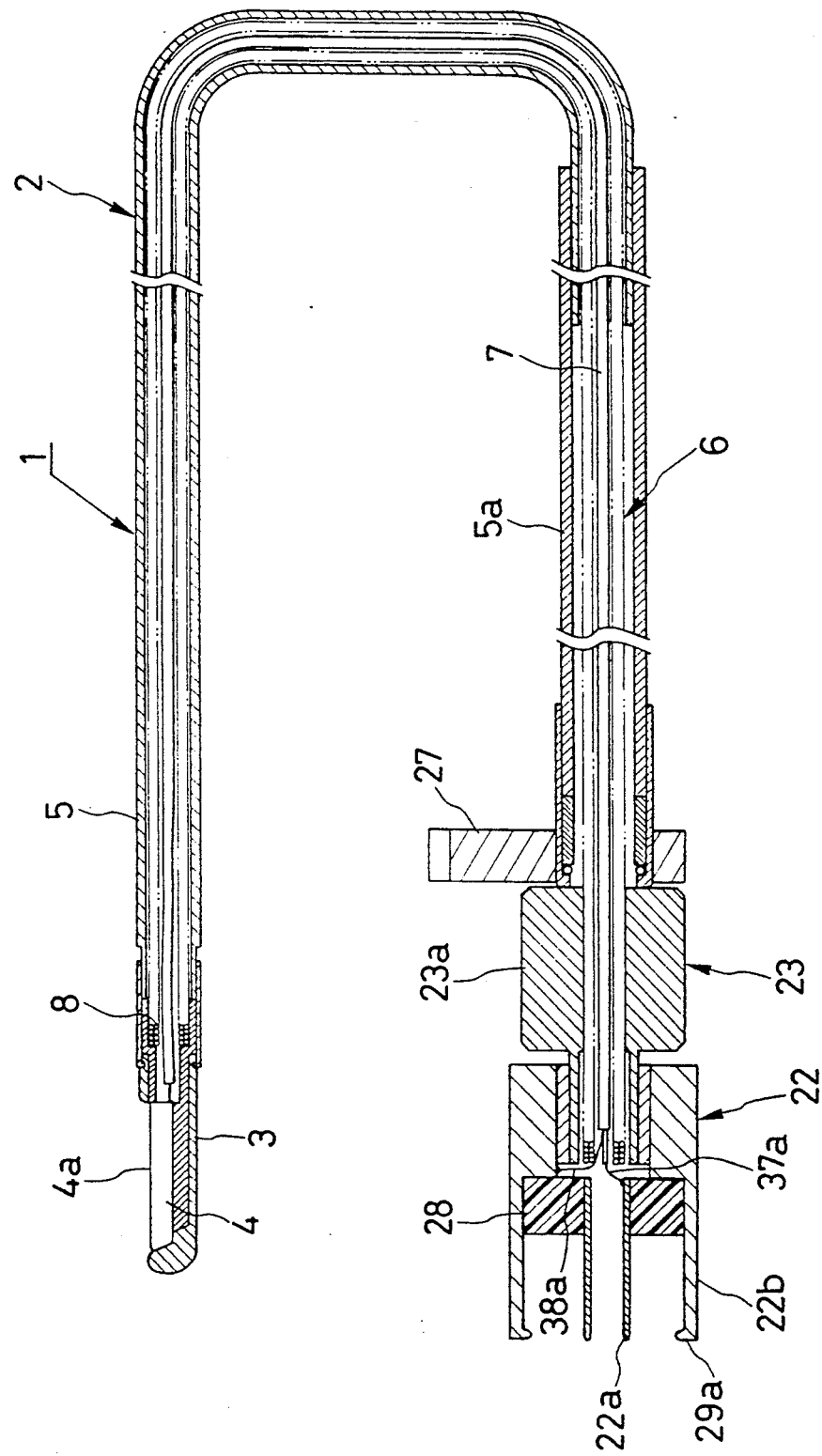
FIG. 2 is a longitudinal section of an insert body of ultrasound probe.

As shown in FIG. 2, the insert body 2 is composed of a flexible tube 5 which is formed of a smooth, flexible material such as fluorine resin or the like to receive the cable 6 therein. The cable 6 electrically connects the ultrasound transducer 4 with the ultrasound image observation terminal T along with the cord 30. The cable 6 has a function of a control cable for turning, through a remote control operation, the rigid tip member 3 on which the ultrasound transducer 4 is mounted. Therefore, the cable 6 is constituted by a coaxial cable which serves as an ultrasound signal line 7, and coil springs 8 which are intimately fitted around the signal transfer line 7 in double layers (or triple layers) to transmit torque to the ultrasound transducer 4. These coil springs 8 are wound in opposite directions relative to each other, and have the respective fore ends securely fixed to the rigid tip member 3 to transmit thereto the torque of manual rotating operation when it is intended to turn the ultrasound transducer 4, in such a manner as to produce substantially the same propelling force in either rotational direction.

Figure 3:
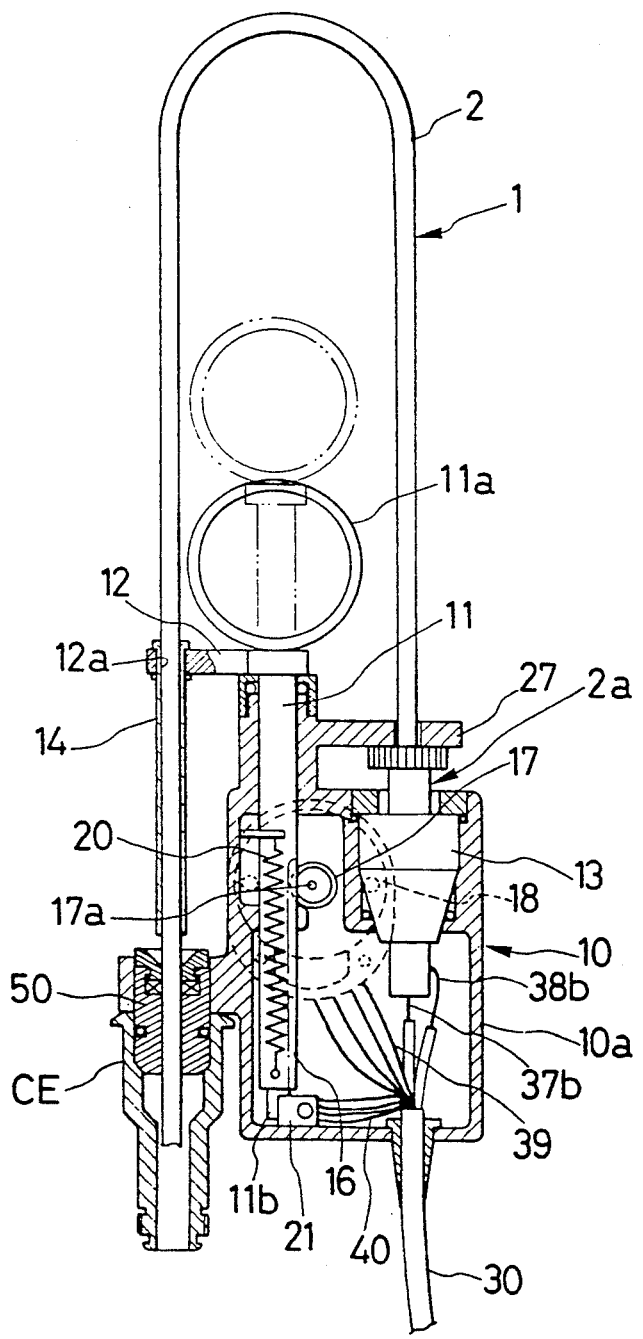
FIG. 3 is a fragmentary sectional view of the ultrasound probe, showing its connections to an operating unit and a rotator mechanism.

The base end of the insert body 2 of the ultrasound probe 1 is detachably connected to the operating unit 10. The ultrasound transducer 4 is scanned over a predetermined range by pulling and pushing the insert body 2 back and forth through the operating unit 10. For this purpose, as shown in FIG. 3, an operating rod 11 is axially slidably provided in a main casing 10a of the operating unit 10, the operating rod 11 having a finger hooker ring 11a at its outer end. Further, the operating rod 11 is securely fixed to a connector arm 12 which is in turn releasably fastened to a proximal portion of the insert body 2, which is loosely folded into a loop-like shape over a predetermined length behind the connector arm 12. At the base end, the insert body 2 is provided with an electrical connector member 2a which is detachably connectible to the main casing 10a. In order to retain the insert body 2 in a loop-like shape between the connector arm 12 and the connector member 2a, a sheathing tube 5a of relatively high rigidity is fitted on the sleeve 5 at the base end portion of the insert body 2 as shown in FIG. 2.

In this connection, the length of the insert body 2 between the connector arm 12 and the connector member 13 is preferred to be sufficient enough for securing smooth axial displacements of the ultrasound transducer 4 over the entire scanning stroke thereof, taking into account the variations in length of the endoscope biopsy channel. In consideration of variations in biopsy channel length between individual endoscopes and in length of protrusion of the ultrasound transducer 4 from the endoscope in scanning operations, the insert body 4 is fixed to the connector arm 12 at a suitable position depending upon the location of the intracorporeal portion to be examined or upon the handiness for the operator. Therefore, the insert body 2 is adjustably fixed to the connector arm 12.

For the purpose of preventing positional deviations of the insert body 2 relative to the connector arm 12 in fixed state, a metal connector pipe 14 is fitted on the insert body 2 within a receptacle hole 12a in the connector arm 12. As shown in FIG. 4, the connector pipe 14 is provided with an axial slit 14a, and an indented wall portion 14b of a smaller diameter providing stepped walls to be engaged with the edge portions of the receptacle hole 12a on the opposite sides of the connector arm 12. Further, the connector pipe 14 is provided with a clamp ring 15 fitted thereon, so that the connector pipe 14 is contracted in diameter upon tightening the clamp ring 15 with a screw 15a, within a range corresponding to the gap width of the slit 14a, thereby clamping the connector pipe 14 to the outer sheath 5a of relatively high rigidity of the insert body 2 to fix the latter securely in position. Accordingly, after sliding the connector pipe 14 to a suitable position along the sheath 5a, its reduced diameter portion 14b is fitted in the receptacle hole 2a in the connector arm 12 to fix the connector pipe 14 thereto, and then the clamp ring 15 is tightened to fasten the connector pipe 14 to the insert body 2, fixing the insert body 2 in an adjusted position relative to the operating rod 11 of the operating unit 10. In this state, the operator puts a finger in the finger hooker ring 11a and pulls or pushes the operating rod 11 in the axial direction, whereupon the insert body 2 including the cable 6 and the rigid tip member 3 is pushed forward or pulled backward through the connector arm 12 to move the ultrasound transducer 4 on the rigid tip member 3 in a desired direction.

While operating the ultrasound transducer 4 in this manner, the return signals are transferred to the ultrasound observation terminal T for signal processing, and displayed on the terminal monitor M as an ultrasound image. In the signal processing, it is necessary to obtain not only the signals concerning the return echoes but also the signals concerning the position of the ultrasound transducer 4. For this purpose, a rack 16 is formed within the casing 10a of the operating rod 11, the rack 10a being meshed with a pinion 17 on a rotational shaft 17a which is connected to an encoder 18 to detect the position of the operating rod 11 from the output signal of the encoder 18. The position signal from the encoder 18 is transferred to the ultrasound observation terminal T.

The operating rod 11 is constantly urged into the position indicated by imaginary line in FIG. 3, by the action of a return spring 20. The operating rod 11 is firstly pushed into the casing 10a by the operator against the biasing action of the return spring 20 into a displaced position indicated by solid line in FIG. 3, and then pulled in outward direction by the operator. By so doing, the ultrasound transducer 4 at the tip end of the insert body 2 is pulled in the direction of retraction into the endoscope S to effect a scan of that range. Further, for the purpose of detecting the end position of the inward stroke of the operating rod 11, a photosensor 21 in the form of a photocoupler or the like is provided within the casing 10a to cooperate with a light shielding plate 11b which is provided at the fore end of the operating rod 11 in detecting the inner stroke end of the operating rod 11 to be used as a reference signal for determining the display end of the ultrasound image on the monitor M of the ultrasound observation terminal T. The positional reference signal from the optical sensor 21 is transferred to the ultrasound observation terminal T along with the output signal of the encoder 18.

Figure 5:
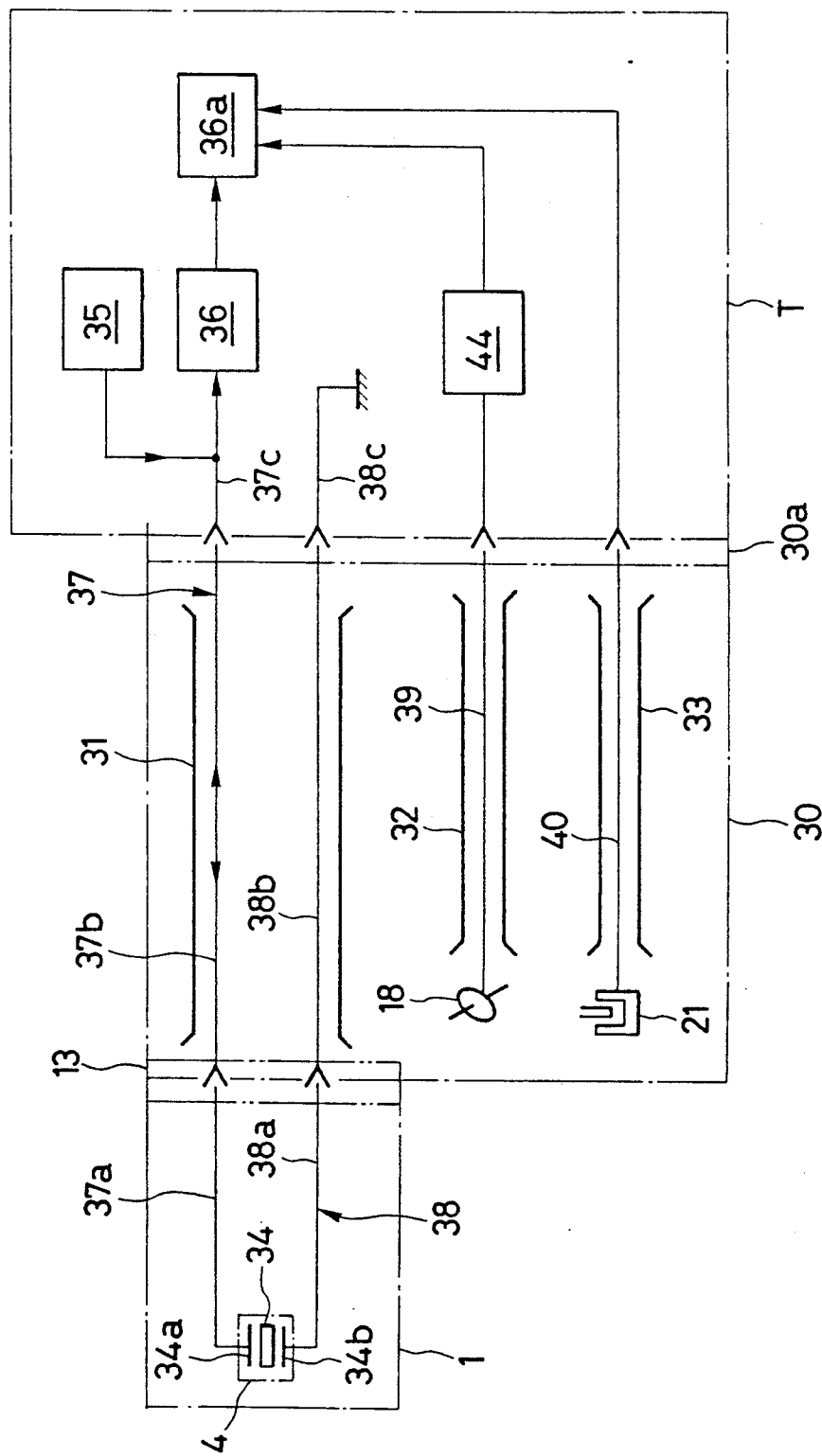
FIG. 5 is a wiring diagram of an ultrasonic signal transmission-reception system.

In this connection, the cord 30 which connects an ultrasound signal transmission-reception line 7 in the insert body 2 with the ultrasound observation terminal T also serves to supply the ultrasound observation terminal T with the signal of the position of the ultrasound transducer 4 from the encoder 18 and the reference position signal from the optical sensor 21. For this purpose, the cord 30 includes an ultrasound signal transfer line 31 which is connected to the ultrasound signal transmission-reception line 7, a position signal transfer line 32 and a reference signal transfer line 33 (FIG. 5). The connector member 2a of the insert body 2 is detachably connectible to an electric connector member 13 which is provided on the side of the casing 10a, and, when connected to the latter, functions to electrically connect the signal line 7 with the ultrasound signal transfer line 31 in the cord 30.

In order to transmit ultrasound energy toward an intracorporeal portion, the ultrasound transducer 4 has to be located in a suitable position and directed toward the target intracorporeal portion. For this purpose, the cable 6 is arranged to be rotatable about its axis within the sleeve 5, permitting remote control of the direction and posture of the ultrasound transducer 4. Nevertheless, the cord 30 which is connected to the ultrasound observation terminal T has to be retained in a fixed state relative to the connector portion 30a (FIG. 5).

Accordingly, when the cable 6 is turned about its axis, it is necessary to prevent transmission of the turning moment to the cord 30 which would otherwise be twisted. To this effect, the cable 6 and cord 30 are connected with each other through a rotary connector 13 which permits relative rotational movements.

As clear from FIG. 2, the connector member 2a of the insert body 2 is constituted by a coupler 22 to be detachably coupled with the rotary connector 13, and a rotator mechanism 23 to be manipulated to turn the rigid tip member 2 with the ultrasound transducer 4 through remote control.

In this instance, the rotator 23 is provided with a rotating ring 23a which can be manually turned with fingers or the like. The rotating ring 23a is fixedly fitted on base end portions of the coil springs 8 which form an outer shell of the cable 6. On the other hand, a fixed arm 27 is connected to the base end of the sheath 5a of the insert body 2, which fixed arm 27 is engaged with an operating rod guide portion 10b of the casing 10a to fix the sheath 5a and the inner sleeve 5 in the rotational direction. Therefore, as the rotating ring 23a is turned with fingers, the coil springs 8 are turned together with the rotating ring 23a, causing the first cable 6 of the signal transfer line 7 to turn about its axis within the sleeve 5.

The coupler 22 is detachably connectible to the rotary connector 13 by a snap action.

Prior to going into the description on the constructions of the coupler 22 and the rotary connector 13, the electric wiring of the ultrasound transmission and reception system is explained below. Namely, as shown in FIG. 5, the ultrasound transmission and reception system includes a transmission circuit 35 which drives the vibratory element 34 of the ultrasound transducer 4 to direct an ultrasound beam to an intracorporeal target, and a reception circuit 36 which receives the echo signals from an intracorporeal structure. The signal lines from these transmission and reception circuits 35 and 36 are integrated at a halfway position into a single transmission-reception line 37 which is connected to one terminal of the vibratory element 34. A grounding wire 38 is connected to the other terminal 34b of the vibratory element 34.

The ultrasound echo signal received by the reception circuit 36 is sent to an ultrasound signal processing circuit 36a to undergo predetermined signal processing. Along with the ultrasound echo signal, the ultrasound signal processing circuit 36a is supplied with a position signal of the ultrasound transducer 4 from the encoder 18 via signal line 39 and comparator 44 which shapes the position signal into pulses, and with a reference position signal from the optical sensor 21 via reference position signal line 40. Based on the ultrasound echo signal, ultrasound transducer position signal and reference position signal, an ultrasound image of scanned intracorporeal tissue is displayed on the terminal monitor M.

More specifically, the signal transmission-reception line 37 and the grounding wire 38 are respectively divided into: wires 37a and 38a provided in the form of a coaxial cable to constitute the ultrasound signal transmission-reception line 7 in the cable 6; wires 37b and 38b provided in the form of a coaxial cable to constitute the signal transfer line 31 incorporated into the cord 30; and wires 37c and 38c on the side of the ultrasound image observation terminal T. The wires 37a and 37b as well as the wires 38a and 38b are connected with each other through the rotary connector 13 which permits relative rotational movements. The other ends of the wires 37b and 38b are detachably connected to the wires 37c and 38c, respectively, through the connector member 30a.

Figure 6:
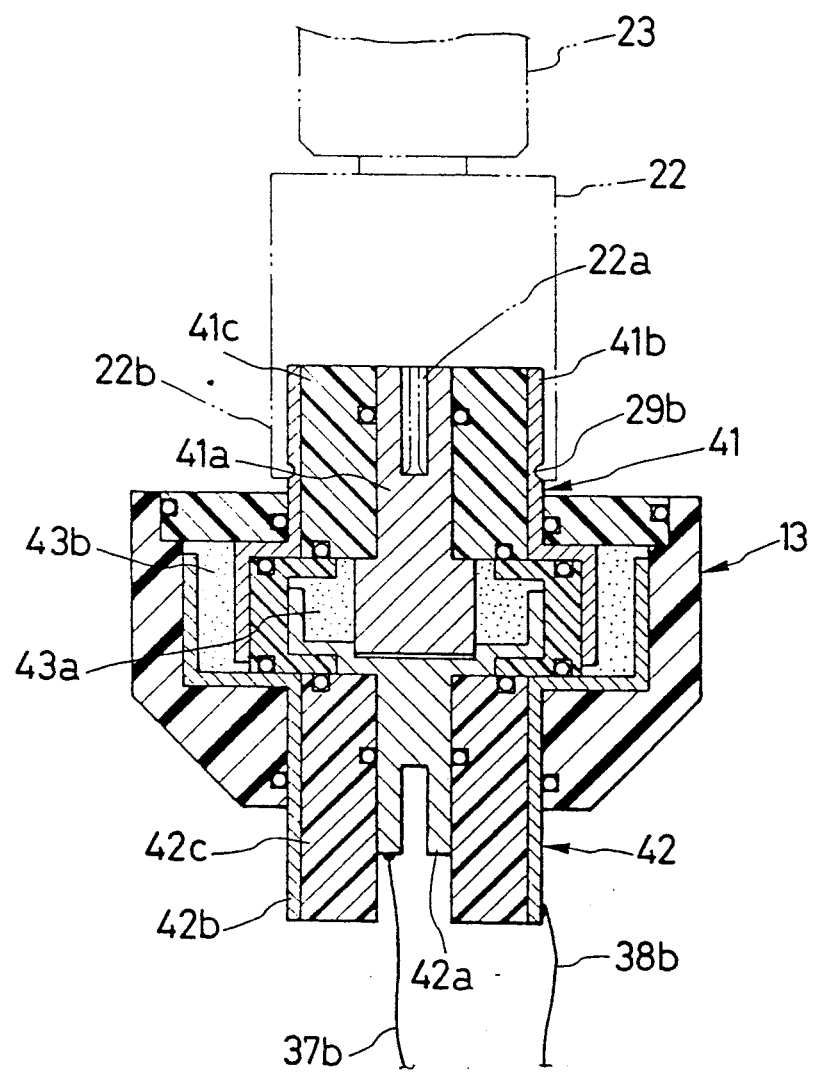
FIG. 6 is a sectional view of a signal transferable rotary connector.

Accordingly, as clear from FIG. 6, the rotary connector 13 is constituted by a rotatable member 41 which is detachably connected to the coupler 22, and a fixed member 42 which is constantly connected to the signal transfer line 31 of the cord 30. The rotatable member 41 is provided with electrodes 41a and 42a to which the wires 37a and 38a are connected, respectively, and which are electrically separated by an insulator 41c. The fixed member 42 is provided with electrodes 42a and 42b to which the wires 37b and 38b are connected, respectively, and which are electrically separated by an insulator 42c. The electrodes 41a and 42a and the electrodes 41b and 42b are connected with each other through a couple of contact portions of mercury, brush or the like.

For the purpose of detachably attaching the cable 6 to the rotary connector 13, the coupler 22 is formed of a pin 22a and a cylindrical member 22b, the pin 22a being connected to the wire 37a of the ultrasound signal transfer line 7 while the cylindrical member 22b is connected to the wire 38a of the signal transfer line 7. An insulating member 28 is interposed between the pin 22a and cylindrical member 22b. Accordingly, the cable 6 can be attached to the rotary connector 13 by fitting the cylindrical member 22b on the electrode 41b of the rotatable member 41 and inserting the pin 22a in the electrode 41a of the rotary connector 13. Further, the coupler 22 is formed with a rib 29a on the inner surface of the cylindrical member 22b, the rib 29a being engageable with a groove 29b on the circumference of the electrode 41b to hold the coupler 22 securely and stably on the rotary connector 13 free of staggering movements or dislocations. As seen in FIG. 1, the sleeve 5 is loosely received in a holder member 50 which securely fixes the operating unit 10 to the rear end CE of a biopsy channel C by way of a locking member 51 which is detachably engageable with the channel end CE.

With the construction as described above, the embodiment of the invention operates in the manner as described below.

In order to make an ultrasound examination or diagnosis by means of the ultrasound-imaging diagnostic system, firstly the endoscope S is inserted into the patient's body until its fore end reaches an intracorporeal portion which needs examination or diagnosis. In this state, the holder member 50 on the front side of the operating unit 10 is fixed to the rear end CE of the biopsy channel C. Thereafter, the insert body 2 of the ultrasound probe 1 is inserted into the biopsy channel C of the endoscope S so that the rigid tip member 3 is protruded out of the fore end of the endoscope S by a predetermined length. The connector pipe 14 which is fitted on the base end portion of the insert body 2 is then fixed to the connector arm 12, and the coupler 22 at the connecting end 2a of the insert body 2 is joined with the rotary connector 13 on the side of the operating unit 10. Further, the fixed arm 27 is connected to the operating rod guide 10b, and the connector member 30a of the cord 30 is connected to the ultrasound observation terminal T.

While observing through the endoscope S, the rigid tip member 3 of the insert body 2 is located in an intracorporeal position to be examined or diagnosed. Then, the rotator mechanism 23 is manipulated to turn the signal transmission-reception surface 4a of the ultrasound transducer 4 toward an intracavitary wall in a predetermined positional relationship therewith.

In this state, by manipulating the finger hooker ring 11a on the operating rod 11, the operating rod 11 is pushed into the casing 10a of the operating unit 10 to block light to the optical sensor 21 with the light blocking plate 11b at the inner end of the operating rod 11. By so doing, it is detected that the ultrasound transducer 4 is located in a scan initiating position, and this is transferred as a reference signal to the ultrasound signal processing circuit 36a through the reference signal transfer line 33. Thereafter, while permitting the operating rod 11 to return under the influence of the action of the return spring 20 or by pulling it back with a finger, ultrasound signals are transmitted and received through the signal transmission-reception surface 4a of the ultrasound transducer 4, the received echo signals being sent to a signal reception circuit 36 through the ultrasound signal line 7 and the signal transfer line 31 in the cord 30 and then to the ultrasound signal processing circuit 36a. Concurrently, the position signal of the ultrasound transducer 4, form the encoder 18, is dispatched to the position signal transfer line 32, and after being shaped into a pulse signal at the comparator 44, supplied to the ultrasound signal processing circuit 36a. After predetermined signal processing through the circuit 36a, an ultrasound image of the intracorporeal tissue under examination is displayed on the terminal monitor M.

In this instance, the insert body 2 is looped in its proximal portion between the connector arm 12 of the operating unit 10 and the coupler 2a to the rotary connector 13, so that, as the insert body 2 is manually pulled back and forth for scanning the ultrasound transducer 4, the looped portion serves to adapt the insert body to the pulling or pushing action without imposing tensile force to the terminal portion connected to the rotary connector 13.

In order to perform the examination or diagnosis in an efficient and accurate manner, the ultrasound transducer 4 on the ultrasound probe 1 need to be located in a proper position with respect to the intracorporeal structure to be examined or diagnosed, facing the transmission-reception surface 4a accurately toward the target structure.

In this regard, the position of the ultrasound probe 1 can be controlled suitably by manipulating the insert body 2 while viewing the probe position through the endoscope S, so that the ultrasound transducer 4 can be located in a position of interest extremely easily and smoothly. However, ultrasound examination or diagnosis of high accuracy cannot be attained simply by locating the ultrasound transducer in a position to be examined or diagnosed. Namely, in a case where the transmission-reception surface 4a of the ultrasound transducer 4 is in a certain relationship with an intracavitary wall, that is to say, in a case where the transmission-reception surface 4a is in intimate contact with an intracavitary wall or intervened by ultrasound transmissive substance like water, it is necessary to orient the transmission-reception surface 4a substantially in parallel relation with the intracavitary wall. As a result, there arises a necessity for controlling the direction and posture of the rigid tip member 3 which supports the ultrasound transducer 4, and this control has to be done with strict accuracy in view of the directionability of the ultrasound.

In order to orient the transmission-reception surface 4a in a particular direction through control of the direction and posture of the ultrasound transducer 4, the rotating ring 23a of the rotator mechanism 23 on the operating unit 10 is turned in a desired direction. By so doing, the cable 6 which is connected to the rotating ring 23a is turned about its axis and twisted as a whole within the sleeve 5a which is secured to the fixed arm 12. Since the fit-on coil springs 8 which sheathe the cable 6 are connected to the rigid tip member 3, they transmit turning moment to the rigid tip member 3, turning same about its axis to turn the transmission-reception surface 4a of the ultrasound transducer into a proper operating direction. At this time, the ultrasound signal line 7 is turned with a fit-on coil spring 8.

The cord 30 which is connected to the ultrasound observation terminal system T is therefore fixed against rotation about its axis. Accordingly, when the cable 6 is turned, the cord 30 might be twisted due to transmission of turning moment. However, since the rotary connector 13 is interposed between the cable 6 and cord 30, the rotation of the rotating ring 23a on the rotator mechanism 23 is transmitted to the rotatable member 41 of the rotary connector 13 through the coupler mechanism 22, idling the rotatable member 41.

Namely, when the rotating ring 23a on the rotator mechanism 23 is turned, the cable 6 and the rigid tip member 3 is turned therewith, accompanied by rotation of the coupler 22 as a whole and of the rotary connector 13, without transmitting rotational force to the side of the fixed portion 42 which is relatively rotatably connected with the rotatable member 41. Accordingly, no twisting force is exerted on the cord 30 with the connector 30a which is connected to the ultrasound observation terminal T.

Consequently, there is no possibility of the ultrasound transducer 4 being spontaneously rotated by righting moment which would otherwise be transmitted to the cord 6 when the cord 30 is twisted. Besides, even if the rotating ring 23a of the rotator mechanism 23 is turned repeatedly in the same direction for the purpose of controlling the direction and posture of the ultrasound transducer 4, the wires between the ultrasound transmitter-receiver 4 and the ultrasound observation terminal T are free from disconnection which might be caused by accumulation of twists.

Thus, there is no need for restricting the rotational angle of the rotating ring 23a of the rotator mechanism 23, which can be turned freely in any direction to provide improved operationability in controlling the direction and posture of the ultrasound transducer 4.

Although the ultrasound probe 1 is shown as being inserted into patient's body through an endoscope in the above-described embodiment, arrangements may be made to insert the ultrasound probe itself into an intracavitary portion to be examined or diagnosed. Further, the rotary connector 13 may be provided at any position between the proximal end of the insert body 2 and the ultrasound observation terminal T. For example, it may be provided on a connector to the ultrasound observation terminal T instead of the operating unit 10. Moreover, the ultrasound transducer may be arranged to be moved in the rotational direction in the scanning operation. Although the rotary connector which is constituted by a slip ring or the like has been shown as having a couple of electrodes on each of its rotatable and fixed sides, it is to be understood that there are no particular restriction on the number of electrodes, which may be determined arbitrarily depending upon the number of wires to be connected by the rotary connector.

What is claimed is:

1. An ultrasound imaging system, comprising:
   an ultrasound probe having an elongated flexible body rotatably supporting an ultrasound transducer on a tip end portion;
   an operating unit including means for scanning said ultrasound probe;
   a flexible cord having one end thereof securely fixed to said operating unit and the other end detachably connected to an ultrasound image observation terminal;
   a rotary connector comprising a rotatable member having at least one rotatable electrode, a fixed member having at least one fixed electrode, and a fluid contact interposed between said rotatable and fixed members to electrically connect said rotatable and fixed electrodes with each other; and
   a cable having a rotatable cable portion one end being fixedly wired to said ultrasound transducer and another end being detachably coupled with said rotatable member of said rotary connector, and a non-rotatable cable portion one end being fixedly wired to said fixed member of said rotary connector and a connector to be connected with said ultrasound image observation terminal.

2. An ultrasound imaging system as defined in claim 1, wherein said ultrasound probe comprises multiple-layer coil springs fitted in a flexible sleeve, said coil springs having fore ends thereof securely fixed to said ultrasound transducer and the rear ends securely fixed to a rotational operating member coupled with said operating unit in such a manner as to permit the operator to torsionally turn said coils within said flexible sleeve by manual operation.

3. An ultrasound imaging system as defined in claim 1, wherein said rotary connector is mounted within a casing of said operating unit.

4. An ultrasound imaging system as defined in claim 3, wherein said ultrasound probe has the base end thereof detachably connected with said rotary connector.

5. An ultrasound imaging system as defined in claim 1, wherein said operating unit comprises an operating rod manually movable in axial direction and releasably connected to a base end portion of said ultrasound probe body to displace same in the axial direction for linearly scanning said ultrasound transducer.

6. An ultrasound imaging system as defined in claim 5, wherein said base end portion of said ultrasound probe body is loosely extended between said operating rod and said operating unit to permit to permit axial forward and backward displacements of said probe body in scanning operation.

* * * * *